(12) United States Patent
Savet

(10) Patent No.: US 6,602,210 B2
(45) Date of Patent: Aug. 5, 2003

(54) DEVICE FOR ANALYSIS OF PROBLEMS WITH THE BALANCE AND POSTURE OF A PERSON

(75) Inventor: Patrick Savet, Blagnac (FR)

(73) Assignee: Patrick Savet SARL, Blagnac (FR)

( * ) Notice: Subject to any disclaimer, the term of this patent is extended or adjusted under 35 U.S.C. 154(b) by 0 days.

(21) Appl. No.: 09/887,095

(22) Filed: Jun. 25, 2001

(65) Prior Publication Data

US 2001/0056249 A1 Dec. 27, 2001

(30) Foreign Application Priority Data

Jun. 23, 2000 (FR) .............................................. 00 08064

(51) Int. Cl.[7] ................................................ A61B 5/00
(52) U.S. Cl. ...................................................... 600/595
(58) Field of Search .................................. 600/587–595

(56) References Cited

U.S. PATENT DOCUMENTS 4,195,643 A    4/1980  Pratt, Jr.
5,551,445 A  * 9/1996  Nashner ...................... 600/595
5,627,327 A    5/1997  Zanakis
5,925,000 A  * 7/1999  Marciniak et al. .......... 600/595
6,063,046 A  * 5/2000  Allum ......................... 600/595

* cited by examiner

Primary Examiner—Max F. Hindenburg
(74) Attorney, Agent, or Firm—Young & Thompson

(57) ABSTRACT

The invention relates to a device for analysis of the posture of a person in orthostatic and/or dynamic conditions, comprising a static force platform (1) which is provided with sensors, which can emit signals which are representative of the position and absolute value of the forces exerted on the said platform by a person in a position of orthostatic balance, a mobile platform (5), which is placed on the static platform (1), and consists of a stand (6) which is secured to means for support (7, 8), which have a lower support surface in the form of a cylindrical section, the area of contact of which with the static platform (1) consists of one of the generatrices of the said lower support surface, which forms the pivot of the said mobile platform, and a unit (9) for acquisition and processing of the signals emitted by the sensors (4) of the static platform (1).

6 Claims, 5 Drawing Sheets

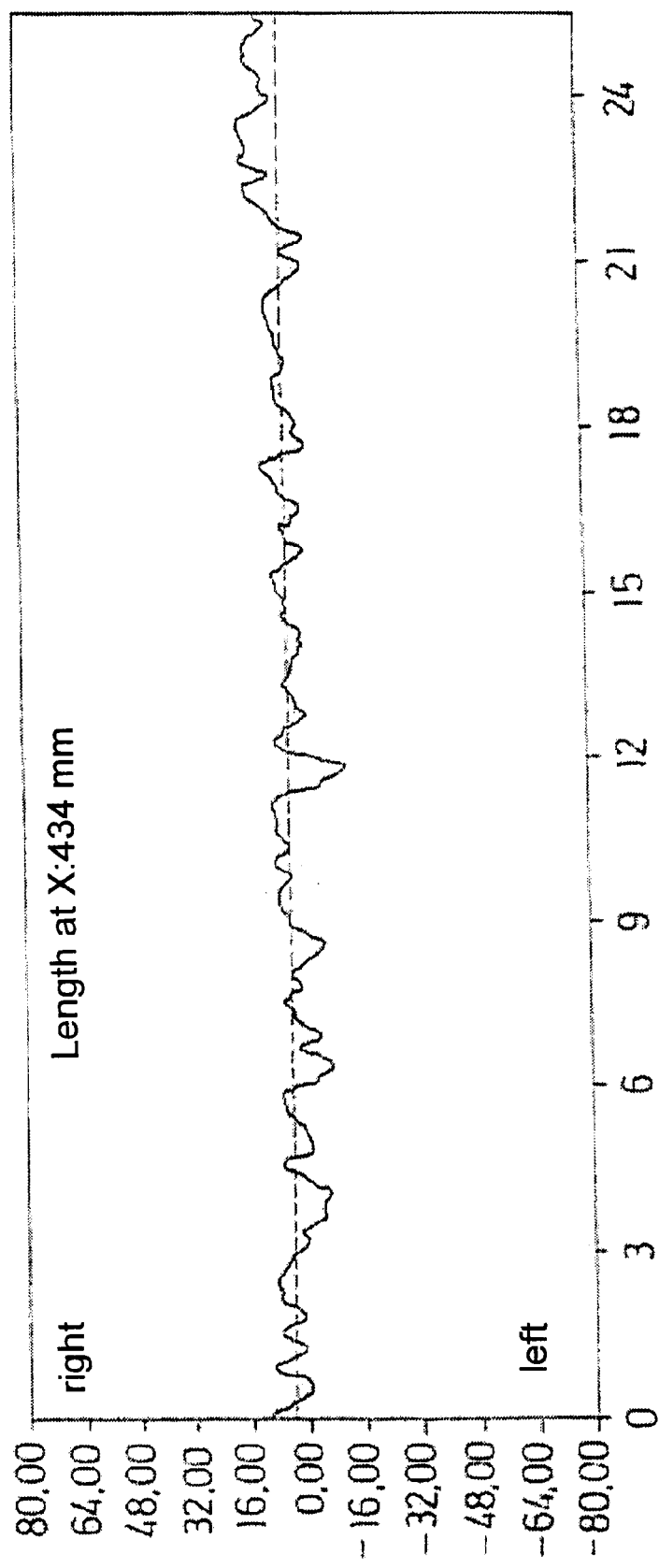

DEVICE FOR ANALYSIS OF PROBLEMS WITH THE BALANCE AND POSTURE OF A PERSON

BACKGROUND OF THE INVENTION

The invention relates to a device for analysis of problems with the balance, and strategies for postural regulation of a person.

It is universally recognised at present by the medical profession that analysis of problems with balance is an excellent tool in particular for assessing and objectifying dysfunctioning of the main neuro-motive and sensorial systems, and also for evaluating the efficiency of rehabilitation therapy of these same systems.

For these reasons, scientists and doctors have developed devices and methodologies for carrying out this analysis. These techniques as a whole are known as clinical posturology, and are aimed at permitting thorough, reliable analysis of the posture of a person in static and dynamic positions.

For this purpose, at present, equipment developed consists of computerised posturology platforms, which make it possible to measure and record the displacement of the centre of pressures of the feet of a person in different examination conditions, which displacement is a direct consequence of the oscillations of the body, which themselves are derived from the quality of regulation of the different neuro-sensorial and neuro-motive systems.

The purpose of the platforms most commonly used is to make it possible to evaluate quantitatively the spontaneous movements of the body of a person in an orthostatic position on a stable base.

For this purpose, the platforms generally consist of static force platforms, comprising a non-deformable stand, which is supported on rigid sensors (strain gauges), which make it possible to analyse the vertical component of the resulting force applied by the weight of the body of a person on the said platforms.

Platforms of this type, connected to a micro-computer, make it possible in particular to provide a plurality of parameters (average X, average Y, length, surfaces, fast FOURIER transformations) which take into account the performance of a person to be kept upright at a given moment, and make it possible to assess the quality of his sensory-motor regulation loops.

The parameters obtained by means of static platforms of this type have proved to be insufficient, owing to the fact that, in everyday life, a patient is rarely in a situation of static balance. For this purpose, and in order to complete the results obtained by means of the static platforms, unstable platforms have been developed, which permit displacements of the sustentation polygon, under the effect of the physiological movements of balancing of the patient, which are thus independent from any external motorisation.

A first type of mobile platform used at present consists of a stand which is supported on a swivel joint or on a shaft (SINGER, BACHMAN, BEGBIE platforms, etc). However, it has been found that when a patient is in place on platforms of this type, his balance is too unstable, and, consequently, he is in danger of falling. Furthermore, maintenance of balance of this type of platform is impossible for pathological patients.

In practice, and for these reasons, mobile platforms of this type are equipped either with stops for limitation of the inclination of the platform, or with a brake, a shock absorber or a spring for slowing down the movement, in order to prevent the patient from falling.

However, the set of stops fragments the continuity of the measurement, and the use of brakes, shock absorbers or springs detracts from the reproducibility of the examination, such that the results obtained by means of platforms of these types are difficult to use, and in no case represent proof of dynamic physiological balance.

In order to eliminate these disadvantages, and to obtain dynamic balance measurement parameters which are easy to compare, one solution consists of providing a mobile platform which creates a spontaneously unstable situation of balance, consisting of a platform, beneath which there is secured a portion of cylinder.

According to this principle, the assembly is supported on the ground by means of a generatrix of the cylinder, and forms a platform with a single degree of freedom of movement. The variation of inclination imposed by the patient in order to maintain his balance is picked up by means of an inclinometer or accelerometer, which provides directly the angular position of the platform relative to the horizontal, which datum is acquired and processed by a micro-computer.

A mobile platform of this type thus permits development by the patient of simple, efficient balance reactions, consisting of rotation associated with translation of the patient on the platform.

Owing to its simplicity, its ease of application, the possibility of distinguishing frontal balance and sagittal balance, and the many parameters which can be exploited, as a complement to static platforms, a mobile platform of this type has been found to constitute an excellent means for evaluation of problems with balance, for objective monitoring of the results of medical or surgical therapy, and for guiding of physiotherapy.

SUMMARY OF THE INVENTION

The object of the present invention is also a device comprising a mobile platform as previously described, and its main objective is to provide a device which is equipped with a platform of this type, which firstly makes it possible to carry out the analysis of the posture of a person, both in orthostatic and dynamic conditions, and secondly, the cost price of which is only slightly higher than that of a static platform alone.

Another object of the invention is to provide a device for analysis which makes it possible to gather an increased number of parameters in dynamic conditions, relative to those gathered by means of the present mobile platforms, and which differentiates the strategies for balancing on the sagittal plane, from the strategies for balancing on the frontal plane.

For this purpose, the invention relates to a device for analysis of the posture of a person, comprising:

a static force platform which is provided with sensors, which can emit signals which are representative of the position and absolute value of the forces exerted on the said platform by a person in a position of orthostatic balance;

a mobile platform, which is placed on the static platform, and consists of a stand which is secured to means for support, which have a lower support surface in the form of a cylindrical section, the area of contact of which with the static platform consists of one of the generatrices of the said lower support surface, which forms the pivot of the said mobile platform; and a unit for acquisition and processing of the signals emitted by the sensors of the static platform, programmed in order to acquire the said signals with a pre-determined frequency, and to proceed with an analysis of the problems with balance and posture of the person, according to frontal and sagittal balance planes, and with frequential analyses of the oscillations created, such as to define the contribution of the different sensory-motor regulation loops, towards maintaining balance in dynamic conditions.

Unlike all the present solutions, which make it necessary to carry out the analyses in orthostatic and dynamic conditions by means of different platforms, each of which is provided with its own measuring sensors and its own unit for acquisition and processing, the invention consists of using the potential provided by the static platforms, such that the latter act as means for measurement which make it possible to evaluate the variations of inclination which a person imposes on a mobile platform, in conditions of dynamic balance.

For an additional cost in relation to a static platform, which corresponds to the cost of a simple mobile platform, the device for analysis according to the invention thus makes it possible to analyse the posture of a person in orthostatic conditions, using the static platform alone, and in dynamic conditions, by placing the mobile platform on the said static platform.

In addition, since the mobile platform is positioned on a static platform, the sensors of the latter make it possible to record not only the variations of the inclination of the said mobile platform, but also the transfers of support, according to an axis which is parallel to the axis of the pivot. Thus, numerous parameters can be exploited in order to take into account performance of balance of a patient, such as:

the length of the path of balance, expressed in mm, degrees or radians;

the maximum amplitude of the oscillations, expressed in mm, degrees or radians;

the average position of the mobile platform, around which the patient is balanced, expressed in mm, degrees or radians;

the vectorial components according to two axes x, y, which are respectively parallel and at right-angles to the axis of the pivot, of the path of balance, which are calculated and represented according to the time (stabilogram at x, and stabiligram at y).

These parameters quantify the ability of the patient to balance in dynamic conditions.

Other parameters also make it possible to take into account individual balance strategies, and to assess the relative contribution of the sensory-motor regulation loops, towards maintaining the balance of the patient.

These parameters are obtained by carrying out a frequential analysis of each stabilogram, by frequency bands, i.e. by calculating the spectral energy of the oscillations, with indication of the distribution of this energy by frequency bands, and as a percentage of the total energy.

With reference to these frequency bands, and advantageously, the unit for acquisition and processing is programmed to proceed with frequential analyses of the oscillations, and their objectivation in three frequency bands, i.e. a band of 0 Hz to 0.5 Hz, a band of 0.5 Hz to 2 Hz, and a band of 2 Hz to 20 Hz.

In fact, the band of 0 to 0.5 Hz corresponds to the slow regulation loops, with a visual and vestibular starting point. The band of 0.5 to 2 Hz corresponds to the regulation loops which are associated with the cerebellar integration. Finally, the band of 2 Hz to 20 Hz corresponds to the fast regulation loops, which are associated with the myotactic reflexes.

According to an advantageous embodiment, the unit for acquisition and processing is programmed in order to acquire the signals emitted by the sensors of the static platform, with a frequency of 40 Hz or more. In fact, frequencies of acquisition of this type make it possible to obtain ideal spectra in a frequency band of 0 to 11 Hz, this last value constituting the fastest physiological trembling of a human being.

In addition, the device according to the invention can be used not only with a patient in a standing position, for the purpose of measurement of his frontal balance and sagittal balance, but also with a patient in a seated position, by positioning and securing the static platform on a support such as a stool.

In this case, in addition, and advantageously, the device comprises a seat with an anatomical shape, the said seat and the mobile platform being provided with means for relative positioning of centring and maintenance of the seat on the mobile platform.

In addition, advantageously, the means for relative positioning of the seat and of the platform comprise a central aperture which is provided in the stand of the said mobile platform, and a centring rod which is secured beneath the said seat, and has a cross-section suitable for being accommodated in the aperture of the said stand.

In addition, according to an advantageous embodiment, the means for support of the stand of the mobile platform consist of two arches with a circular section, disposed laterally beneath the said stand.

BRIEF DESCRIPTION OF THE DRAWINGS

Other characteristics, objects and advantages of the invention will become apparent from the following detailed description, provided with reference to the attached drawings, which represent a preferred embodiment, by way of non-limiting example. In these drawings:

FIGS. 5a to 5c are diagrams which represent some of the operating parameters obtained by means of a device for analysis according to the invention.

Figure 1:
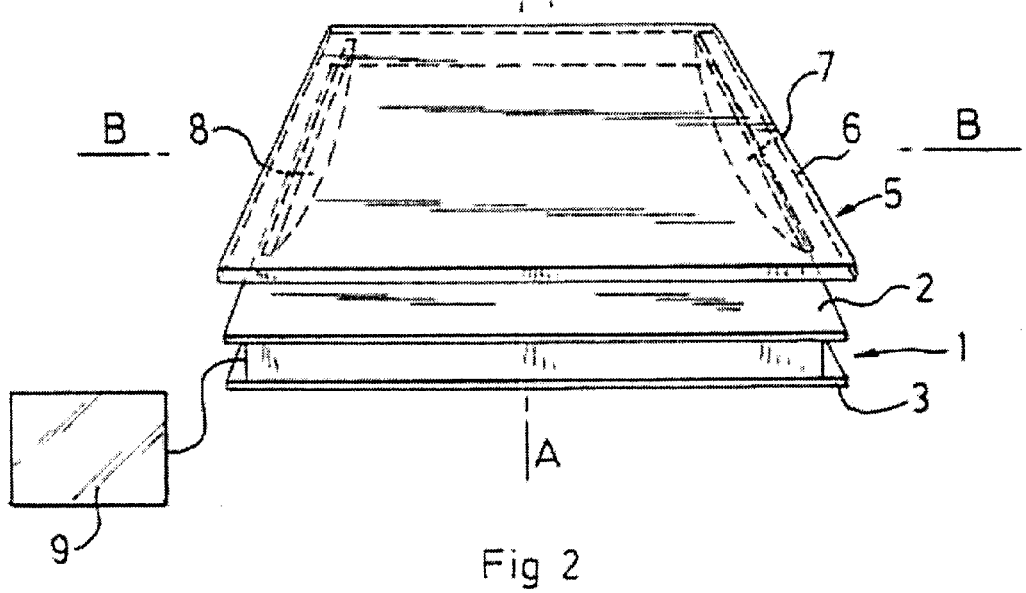
FIG. 1 is a perspective view of a device according to the invention, for analysis of the posture of a person standing.
Figure 2:
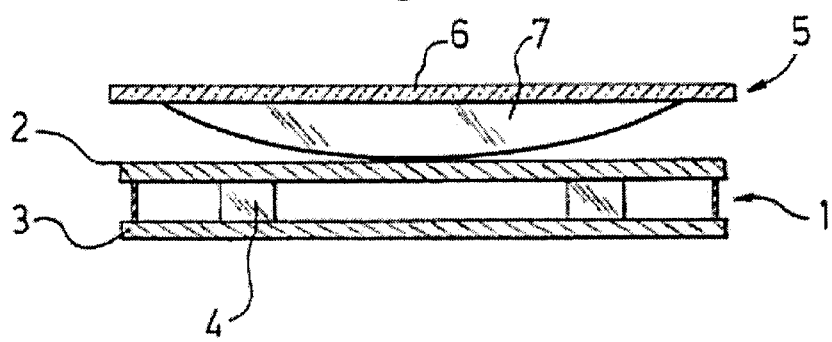
FIG. 2 is a transverse cross-section through a plane A of this device for analysis.
Figure 3:
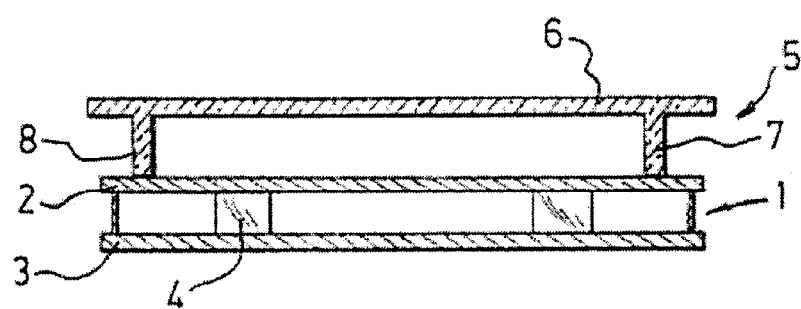
FIG. 3 is a transverse cross-section through a plane B.

The device for analysis of the posture of a person shown in the figures is designed to make it possible to carry out this analysis in orthostatic conditions and in dynamic conditions, with the possibility in the second case of measuring the frontal balance and sagittal balance of the person.

This device comprises firstly a static platform 1, consisting of two parallel square stands 2, 3, between which there are disposed three sensors such as 4, of the constant moment beam type, which are uniformly distributed around the axis of the said stands. A static platform 1 of this type, when used alone, makes it possible to analyse in a conventional manner the posture of a person in orthostatic conditions, and is connected for this purpose to a micro-computer 9 for acquisition and processing of the signals emitted by the sensors.

The device additionally comprises a mobile platform 5, which is designed to be positioned on the static platform 1.

This mobile platform 5 consists of a square stand 6, beneath which there are secured two lateral arches 7, 8, which have a radius of curvature of 55 cm, and a camber of 6 cm, which provide the said platform with a single degree of inclination.

Figure 5A:
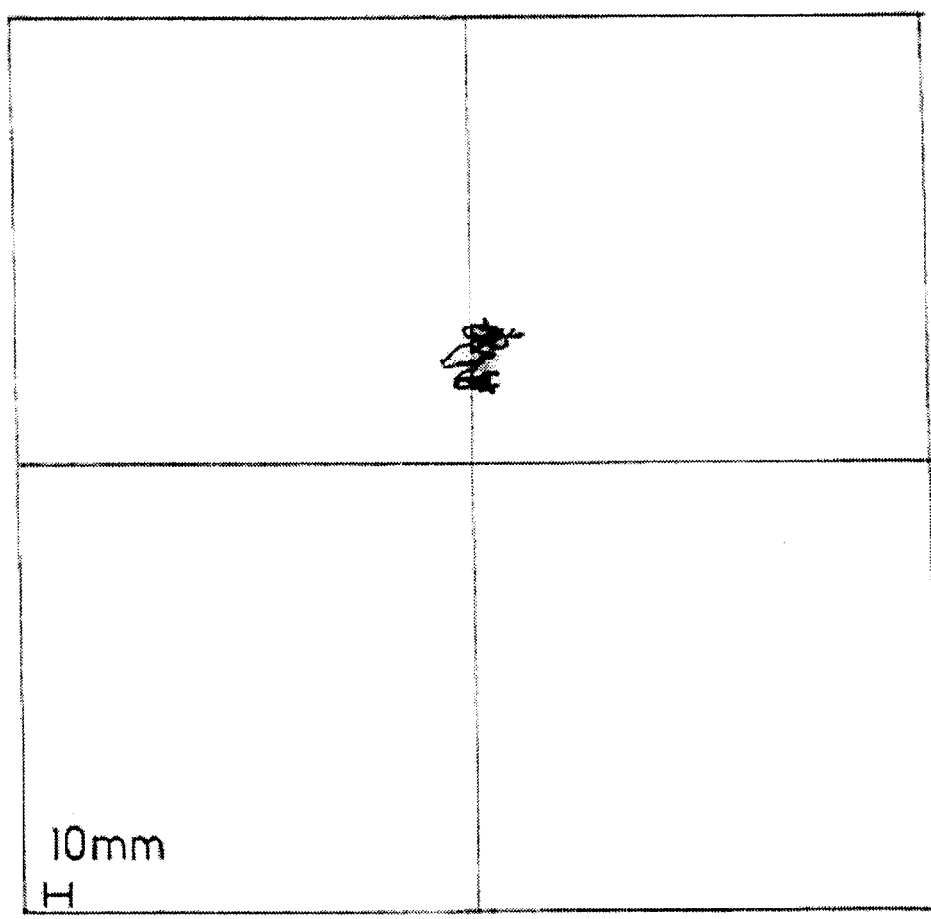
Figure 5C:
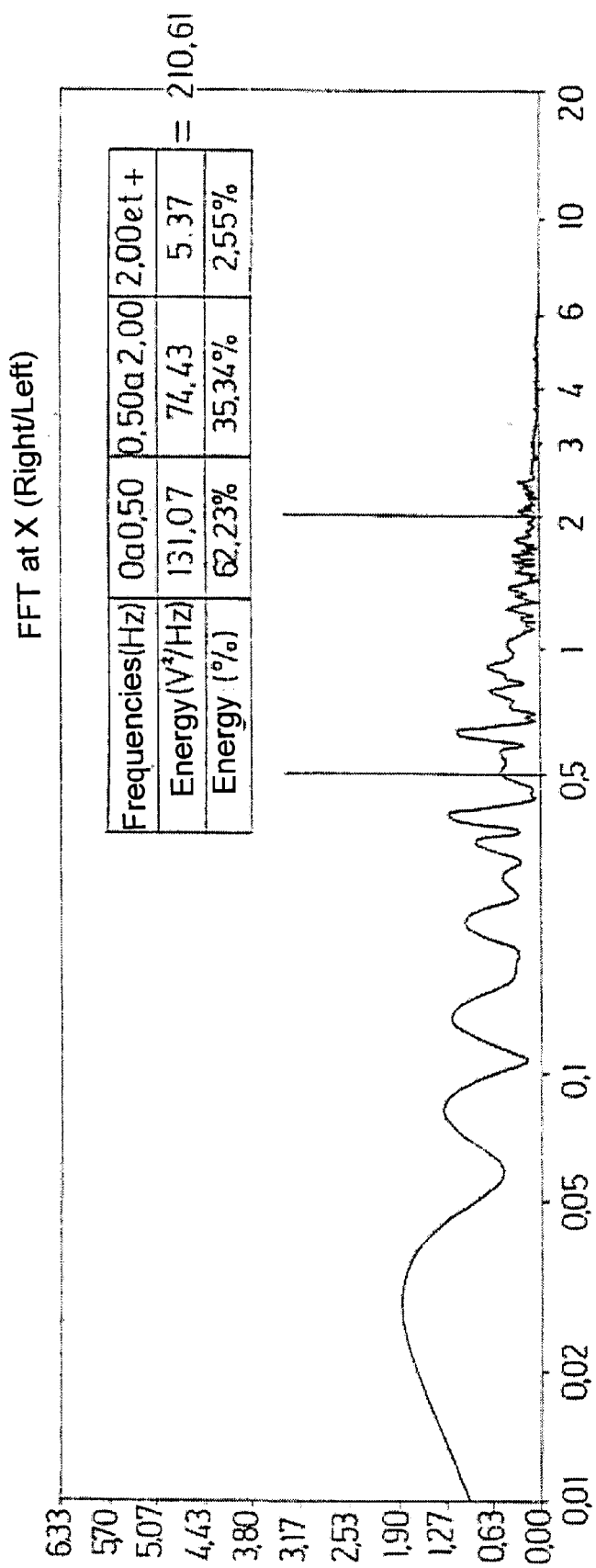

During an examination session which is designed to evaluate either the frontal balance or the sagitral balance of a person, the signals emitted by the sensors 4 are acquired by the micro-computer 9 with a frequency of 40 Hz, then are processed such as to supply the following parameters which can be exploited:

length of the path of balance, with potting of the latter, as represented by way of example in FIG. 5a, the said path and the said plotting corresponding to the successive sampled positions of the center of pressure;

the maximum amplitude of the oscillations;

the average position of the mobile platform 5 around which the patient is balanced;

the vectorial components at x and y of the path of balance which are calculated and plotted (stabilogram at x and y) according to the time, as shown by way of example in FIG. 5b; and the results of the spectral analysis (fast FOURIER transformations of each stabilogram, which make it possible to calculate the total energy of the spectrum, and the energy by frequency bands. By way of example, figure cc represents plotting of these results, which shows that three frequency bands are being studied, i.e. respectively 0–0.5 Hz, 0.5–2 Hz, 2–20 Hz.

The device according to the invention can also be used such as to carry out the measurements with patients in a seated position, in dynamic conditions, with their feet dangling or placed on a step, for the purpose of evaluation and proprioceptive rehabilitation of the rachis.

Figure 4:
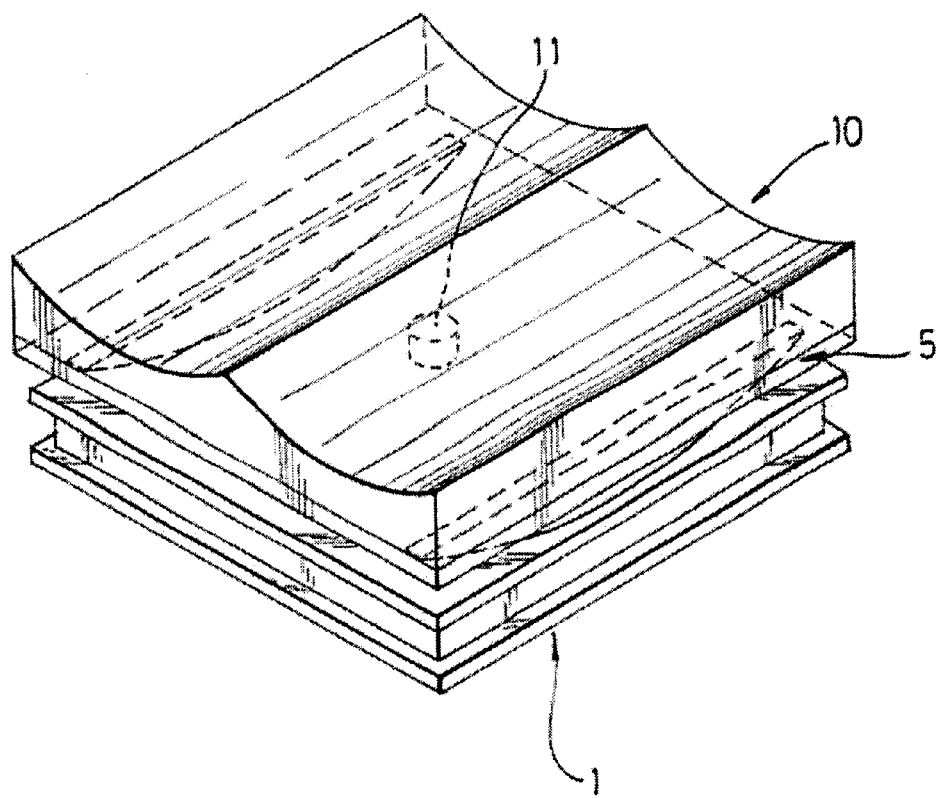
FIG. 4 is a perspective view of a device according to the invention, for analysis of the posture of a person in a seated position.

For this purpose, the device must be placed and secured on a stool. In addition, as represented in FIG. 4, for ergonomic purposes, a seat 10 with an anatomical shape is placed on the stand 6 of the mobile platform 5.

In addition, in order to assure the positioning of this seating 10, the latter comprises a centring rod 11 which is secured beneath the said seat, and is designed to be accommodated in an axial aperture provided in the stand 6.

What is claimed is:

1. A device for analysis of the posture of a person in orthostatic and/or dynamic conditions, comprising:

a static force platform having a plurality of sensors, said plural sensors emitting signals which are representative of a position and absolute value of forces exerted on the static platform by a person in a position of orthostatic balance;

a mobile platform, which is placed on the static platform, and consists of a stand which is secured to means for support, said means for support having a lower support surface in the form of a cylindrical section, an area of contact of the cylindrical section with the static platform consists of a generatrix of the lower support surface, said generatrix forming a pivot of the mobile platform; and a unit for acquisition and processing of the signals emitted by the sensors, said unit being programmed in order to acquire said signals with a pre-determined frequency, and to proceed with an analysis of the problems with balance and posture of the person, according to frontal and sagittal balance planes, and with frequential analyses of the oscillations created, so as to define the contribution of the different sensory-motor regulation loops, towards maintaining balance in dynamic conditions.

2. A device for analysis as claimed in claim 1, wherein the means for support of the stand of the mobile platform consist of two arches having a circular section, disposed laterally beneath the stand.

3. A device for analysis as claimed in claim 1, wherein the unit for acquisition and processing (9) is programmed in order to acquire the signals emitted by the sensors (4) of the static platform (1), with a frequency of 40 Hz or more.

4. A device for analysis as claimed in claim 1, wherein the unit for acquisition and processing (9) is programmed to proceed with objective frequential analyses of the oscillations, in three frequency bands, i.e. a band of 0 to 0.5 Hz, a band of 0.5 Hz to 2 Hz, and a band of 2 Hz to 20 Hz.

5. A device for analysis of the posture of a person in orthostatic and/or dynamic conditions, comprising:

a static force platform having a plurality of sensors, said plural sensors emitting signals which are representative of a position and absolute value of forces exerted on the static platform by a person in a position of orthostatic balance;

a mobile platform, which is placed on the static platform, and consists of a stand which is secured to a support having a cylindrical lower support surface, an area of contact of the cylindrical support surface with the static platform including a generatrix of the lower cylindrical support surface, said generatrix forming a pivot of the mobile platform;

a seat with an anatomical shape, said seat and said mobile platform having means for relative positioning or centering and maintenance of the sear on the mobile platform; and a unit for acquisition and processing of the signals emitted by the sensors, said unit being programmed in order to acquire said signals with a pre-determined frequency, and to proceed with an analysis of the problems with balance and posture of the person, according to frontal and saoirrai balance pianos.

6. A device for analysis as claimed in claim 5, wherein the means for relative positioning of the seat (10) and of the platform (5) comprise a central aperture which is provided in the stand (6) of the said mobile platform, and a centring rod (11) which is secured beneath the said seat, and has a cross-section suitable for being accommodated in the aperture of the said stand.

* * * * *